(12) United States Patent
Campás et al.

(10) Patent No.: US 10,149,630 B2
(45) Date of Patent: Dec. 11, 2018

(54) FERROFLUID DROPLETS AS IN SITU MECHANICAL ACTUATORS AND RHEOMETERS IN SOFT MATERIALS AND BIOLOGICAL MATTER

(71) Applicant: The Regents of the University of California, Oakland, CA (US)

(72) Inventors: Otger Campás, Goleta, CA (US); Friedhelm Serwane, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 106 days.

(21) Appl. No.: 14/923,078

(22) Filed: Oct. 26, 2015

(65) Prior Publication Data

US 2016/0116394 A1 Apr. 28, 2016

Related U.S. Application Data

(60) Provisional application No. 62/073,012, filed on Oct. 31, 2014, provisional application No. 62/068,870, filed on Oct. 27, 2014.

(51) Int. Cl.
*G01K 13/02* (2006.01)
*A61B 5/05* (2006.01)
*A61B 5/00* (2006.01)
*G01N 11/00* (2006.01)
*G01N 15/00* (2006.01)
(Continued)

(52) U.S. Cl.
CPC ............ *A61B 5/0515* (2013.01); *A61B 5/441* (2013.01); *G01N 15/1425* (2013.01); *G01N 15/1463* (2013.01); *G01N 11/00* (2013.01);

*G01N 15/147* (2013.01); *G01N 2011/0086* (2013.01); *G01N 2015/0065* (2013.01);
(Continued)

(58) Field of Classification Search
CPC ........................................................ H01F 1/44
See application file for complete search history.

(56) References Cited

U.S. PATENT DOCUMENTS 3,916,419 A * 10/1975 Fan ........................... B41J 2/06
346/74.2
4,928,125 A * 5/1990 Iino ........................... B41J 2/06
347/100

(Continued)

OTHER PUBLICATIONS

E.K. Ruuge and A.N. Rusetski, "Magnetic Fluids as Drug Carriers: Targeted Transport of Drugs by a Magnetic Field," Journal of Magnetism and Magnetic Materialsm, vol. 122, Issues 1-3 (Apr. 1993), pp. 335-339.

(Continued)

*Primary Examiner* — Harshad R Patel
*Assistant Examiner* — Tran M Tran
(74) *Attorney, Agent, or Firm* — Mountain IP, pLLC

(57) ABSTRACT

Presented herein are methods of using ferrofluid droplets as mechanical actuators that work across length scales of nanometers to millimeters. These novel actuators and methods of using them can be used to determine mechanical properties of soft materials. The actuators allow calculation of a soft material's viscosity, elastic modulus, and other mechanical properties. The methods and devices of the invention may be employed in biological materials, including live cells and tissues, and may be used to profile the mechanical properties of such living materials or to manipulate biological processes therein.

3 Claims, 4 Drawing Sheets

(51) Int. Cl.
   *G01N 15/14*   (2006.01)
   *G01N 15/10*   (2006.01)

(52) U.S. Cl.
   CPC .............. *G01N 2015/1006* (2013.01); *G01N 2015/1495* (2013.01); *G01N 2203/0089* (2013.01)

(56) References Cited

U.S. PATENT DOCUMENTS

| | | | | |
|---|---|---|---|---|
| 6,290,894 | B1* | 9/2001 | Raj | G09B 23/181 |
| | | | | 264/405 |
| 6,408,884 | B1* | 6/2002 | Kamholz | B01L 3/50273 |
| | | | | 137/251.1 |
| 6,415,821 | B2* | 7/2002 | Kamholz | B01L 3/50273 |
| | | | | 137/251.1 |
| 7,022,077 | B2* | 4/2006 | Mourad | A61B 5/0048 |
| | | | | 600/449 |
| 7,204,581 | B2* | 4/2007 | Peeters | B01L 3/0268 |
| | | | | 137/827 |
| 7,494,482 | B2* | 2/2009 | Orgill | A61L 15/42 |
| | | | | 424/423 |
| 8,528,589 | B2* | 9/2013 | Miller | B01L 3/0241 |
| | | | | 137/487.5 |
| 2012/0275929 | A1* | 11/2012 | Salsman | F04B 43/04 |
| | | | | 417/53 |

OTHER PUBLICATIONS

Chenjie Xu and Shouheng Sun, "New Forms of Superparamagnetic Nanoparticles for Biomedical Applications," Advanced Drug Delivery Reviews 65, (2013), pp. 732-743.

Jung-Tak Jang, Hyunsoo Nah, Jae-Hyun Lee, Seung Ho Moon, Min Gyu Kim, and Jinwoo Cheon, "Critical Enhancements of MRI Contrast and Hyperthermic Effects by Dopant-Controlled Magnetic Nanoparticles," Agnew.Chem 2009, pp. 12690-1264. 2009 Wiley-VCH Verlag GmbH & Co., KGaA, Weinheim.

Bruno Ando, Salvatore Baglio and Angela Beninato, "Magnetic Fluids for Bio-medical Application," DIEES, Engineering Faculty of Catania, Adv. in Biomedical Sensing, LNEE 55, pp. 16-28. Springer-Verlag, Berlin Heidelberg, 2010.

Kevin Zimny, Benoit Mascaro, Thomas Brunet, Oliver Poncelet, Christopher Aristegui, Jacques Leng, Olivier Sandre, and Olivier Mondain-Monval, "Design of a Fluorinated Magneto-Responsive Material with Tuneable Ultrasound Scattering Properties," Published Jan. 3, 2014. Journal of Materials Chemistry B, issue 10.

* cited by examiner

FERROFLUID DROPLETS AS IN SITU MECHANICAL ACTUATORS AND RHEOMETERS IN SOFT MATERIALS AND BIOLOGICAL MATTER

CROSS-REFERENCE TO RELATED APPLICATIONS

This application claims the benefit of U.S. Provisional Application No. 62/068,870, filed Oct. 27, 2014 and U.S. Provisional Application No. 62/073,012, filed Oct. 31, 2014, which are hereby incorporated by reference, in their entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

Major technological benefits have been enabled by the ability to explore and engineer systems with controlled mechanical properties across multiple length scales. A prime example is the Eiffel tower in Paris consisting of mechanical elements at three distinct length scales thus achieving an unprecedented degree of stability. This concept of hierarchical mechanical properties has been transferred to research new microstructures with enhanced physical properties such as polymer gels, foams and biological materials such as bones, cells and tissues.

However engineering systems in the micron to mm scale is extremely challenging due to the lack of techniques to accurately measure the mechanical properties locally within the material, at the abovementioned scales. Currently it requires a combination of conventional techniques such as bulk rheology (mm scale) with e.g. atomic force microscopy (micron scale). This has severe drawbacks as (a) not all intermediate length scales can be probed and (b) only some techniques are compatible with living materials such as cells and tissues. In particular there is no technique to probe the mechanics of living tissues and/or cells as these develop in embryos, adult organisms and disease processes, spatially in the micron to mm range. Also, it would be very useful to be able to measure the spatiotemporal mechanical properties of soft materials (whether inert or living), as these measurements would allow the connection of the local mechanical properties and structure at the microscale with the mesoscopic and macroscopic mechanics of the system. The mechanical (material) properties of the cellular microenvironment are physical quantities that control cell behavior. The compliance or fluidity to which cells are exposed acts as a signal that can affect critical cells behaviors, for example, cell differentiation and regulation of tumor progression. Currently, there is no available technique to quantify the local mechanical properties of the cellular microenvironment. The mechanical behavior of cellular aggregates has been studied in vitro by micropipette aspiration and microindentation techniques. Unfortunately, these techniques cannot be used in vivo, inside developing embryos and in disease processes in living organisms. Laser ablation has been used to estimate the mechanical properties of living tissues, but cannot provide a quantitative measure because the forces driving tissue relaxation are unknown. Only optical tweezers have been recently used at sub cellular scales to measure the mechanical properties of the cell cortex. None of the mentioned techniques allows the precise application of controlled forces at the necessary spatial and temporal scales to quantify cellular and tissue mechanics during embryonic development, adult organs and/or disease processes (such as tumor progression).

SUMMARY OF THE INVENTION

Herein is presented a new methodology that allows for the direct quantitative measurement of the local mechanical properties of living and non-living soft materials across multiple length scales and different spatial directions (anisotropy). The technique enables, for the first time direct quantification of the spatiotemporal mechanical behavior (including anisotropy) of living tissues and organs, as well as soft inert materials (such as polymer melts, emulsions, foams, etc.). The methods of the invention utilize ferrofluid droplets as mechanical actuators in non-living and living materials. In the latter case, biocompatible droplets are used to probe the mechanics of the system at intracellular level, cell level and/or tissue level. By applying a controlled, spatially uniform magnetic field to magnetic ferrofluid droplets, precise forces can be applied within the sample. The application of spatially uniform magnetic fields to a magnetic drop induces its deformation, but not its movement. The drop deformation generates forces on the material in which it is embedded (similar to a force dipole). By applying gradients of magnetic field on the magnetic drop, it is also possible to apply net forces on the drop and control its movement. Actuation at different length scales (to measure the mechanical properties of the material at different length scales), from micron scale to millimeter scale (and larger if necessary), is achieved by varying the size of the ferrofluid drop used for mechanical actuation. The temporal evolution of the droplet deformation in response to the application of controlled magnetic stresses provides a readout of the mechanical properties of the material surrounding the ferrofluid drop. By monitoring the drop shape changes over time, the local mechanical behavior of the material surrounding the drop can be determined. The methods and compositions of the invention may also be utilized in non-biological contexts, allowing for the mechanical characterization of any soft material, being any material that can be deformed (even if slightly) by the mechanical stresses applied by the ferrofluid drop embedded in it when actuated with an externally applied magnetic field. The invention encompasses the ferrofluid materials, methods of placing them within target materials, methods of applying forces to the droplets, methods of measuring physical and material properties of the environment surrounding the droplet, methods of measurement of the material or mechanical properties (such as interfacial tension) of the ferrofluid droplet itself, software to perform all these measurements and analysis, and apparatuses for applying forces and measuring droplet deformation.

DETAILED DESCRIPTION OF THE INVENTION

1. Ferrofluid Liquids

Figure 1A:
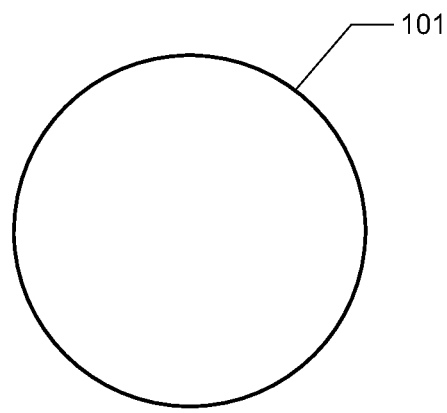
FIG. 1A depicts a ferrofluid droplet (101) in a target material wherein no magnetic field is applied, and the droplet is essentially spherical.

Carrier Liquid. In one aspect, the invention comprises novel ferrofluid liquids which may be used as tools in material characterization. Ferrofluid liquids comprise at least two components—a carrier liquid and a magnetic component. The carrier liquid is a liquid that will maintain a stable conformation, such as a droplet, when placed within the target material, and with low enough interfacial tension (at the temperature of the target material) to change in shape in response to externally applied magnetic fields. The carrier liquid will preferably be substantially immiscible and chemically inert in the environment in which it is placed. In the case of biological samples, the chemical environment consists of a significant amount of hydrocarbon molecules and other molecules which are water-soluble. Therefore, for such applications, the carrier fluid must be an oil or other liquid which is neither soluble in hydrocarbon oils nor in water-based solutions.

In some embodiments, the carrier fluid comprises an oil. Oils are especially amenable to biological uses, as they can be sufficiently hydrophobic to persist in the aqueous environment of a biological system without dissolving, dispersing, or interacting with the surround material. Exemplary oils suitable for use in biological applications include fluorocarbon oils, silicone oils and mineral oils, among others. Essentially, any biocompatible oil could be used.

In one embodiment, the carrier fluid of the invention is a fluorocarbon oil. Any organofluorine oil which is substantially liquid (at the temperature of the target material) and which is substantially not miscible with the fluidic environment of the target material may be used. Exemplary fluorocarbon oils of the invention include the series of electronic fluids developed by 3M, including Pentane, 1,1,1,2,2,3,4,5,5,5-decafluoro-3-methoxy-4-(trifluoromethyl), sold as NOVEC 7500(™), and 3-ethoxy-1,1,1,2,3,4,4,5,5,6,6,6-decafluoro-2-trifluoromethyl-hexane, sold as NOVEC 7300 (™). 3M also produces an oil called FC70, the composition of which is not disclosed, beyond that it contains perfluoro compounds, primarily compounds with 15 carbons. Other commercial or non-commercial fluorocarbon oils or fluids can also be used.

Magnetic Component. The ferrofluid droplets also comprise a magnetic component. The magnetic component is typically dissolved, dispersed, suspended or otherwise present within the carrier fluid. The magnetic component comprises any magnetic material, or combination of materials, that can be dissolved or dispersed within the carrier fluid and which will impart substantial magnetization to a droplet or other body comprising the carrier fluid. Exemplary magnetic materials include ferrous, ferromagnetic, ferrimagnetic, paragmagnetic, and superparamagnetic materials. Exemplary magnetic materials include iron (including iron oxides), nickel, cobalt, rare earth magnetic materials such as Neodymium, organometallic compounds, or alloys of the foregoing. Exemplary magnetic materials comprise maghemite and magnetite.

In a preferred implementation, magnetic particles or nanoparticles are used. The particle size should be at least two orders of magnitude smaller than the droplet in which it will be placed, for example 3, 4, 5, or 6 orders of magnitude smaller. For example, depending on the application, particles having diameters of 1 to 1000 nm may be used. Particles of less than 100 nm in diameter, for example having diameters from 5-20 nm, are preferred in many embodiments. Although the saturation magnetization is not affected by the particle size, the magnetic susceptibility increases with increasing nanoparticle diameters. The diameter of the nanoparticle may range, for example, from 1 nm to 1000 nm, depending on the application. For most applications particle diameters of d<100 nm are desirable, in particular for biological applications. Particle diameters from 7 nm to 20 nm are suitable, as they show a large enough magnetic susceptibility while remaining small compared to the size of the oil droplets.

The magnetic materials, if not readily dissolved or dispersed within the carrier liquid, may further comprise a compatibility coating or surface modification (either surfactants or other surface chemical treatment) to aid in their dissolving or dispersion within the carrier liquid. For example, if the carrier liquid is a fluorocarbon oil and the magnetic component is an iron-based nanoparticle (such as iron oxides or doped iron oxides), the iron-based nanoparticle may be modified with surface fluorocarbon groups such that it dissolves within the fluorocarbon oil. If the carrier liquid is silicone oil, silicone surfactants or other chemical groups with affinity to silicone can be used to modify the nanoparticles and enhance their solubility in the carrier fluid.

The magnetic material may be loaded into the carrier liquid at any density, preferably at a density that does not substantially affect the viscosity of the carrier liquid. Exemplary loading densities of 0.1 to 15% by volume may be used, for example in the range of 5-7%.

In general, it is important that the interfacial tension of the liquid be small enough in order that droplets of the ferrofluid liquid be readily deformed by the application of external magnetic fields. For example, ferrofluid droplets having an interfacial tension in the range of 1 to 30 mN/m are preferred. However, ferrofluid drops with lower and higher interfacial tensions can also be used, as long as the magnetic properties of the ferrofluid (i.e., the magnetic nanoparticles or other dissolved magnetic particles) and/or the applied magnetic field are adjusted so as to deform the drop. The carrier liquid may further comprise surfactants to modify the interfacial tension of the carrier liquid with the target material. For example, in a fluorocarbon-based ferrofluid, fluorinated PEG surfactant may be used to lower the interfacial tension of droplets to about 3 mN/m when the drop is immersed in water. Other surfactants, including colloidal particles or molecules with a fluorocarbon moiety, can be used to lower the interfacial tension of the fluorocarbon-based ferrofluid drop when in contact with other fluids.

Imaging of magnetic droplets. Even very small deformation of the droplets can be detected, with a variety of techniques. One possibility is ultrasound scattering as done in ZIMNY ET AL. Design of a fluorinated magneto-responsive material with tuneable ultrasound scattering properties, J. Mater. Chem. B, 2014, 2, 1285-1297. Also, spectral detection techniques based on the modes of a laser are possible as done in HUMAR et al. Nature Photonics 9, 572-576 (2015). Alternatively microscopy techniques can be used. Here, the droplets can be imaged on any standard inverted microscope using simple bright-field illumination. Modification of droplets can also be made so that they are visible using fluorescence imaging, which is especially useful when used in living materials and living systems, such as in living tissue, cell aggregates and inside individual cells. To obtain fluorescent oil droplets the, fluorocarbon oil can be mixed with fluorinated fluorescent dye, for example the dye described in SLETTEN ET AL, FLUOROFLUOROPHORES: FLUORESCENT FLUOROUS CHEMICAL TOOLS SPANNING THE VISIBLE SPECTRUM. JOURNAL OF THE AMERICAN CHEMICAL SOCIETY, 136(39): 13574-13577, 2014. PMID: 25229987. Other fluorescent dyes can be used as long as they can be dissolved in the liquid carrier of the ferrofluid. In the case of an aqueous based ferrofluid, a variety of commercially available dyes can be used for fluorescence imaging, such as the Alexa Fluor® dyes (Invitrogen). Also, the liquid carrier itself be autofluorescent and used for fluorescent imaging.

The liquid carrier itself can also be used as contrast agent for imaging with other imaging techniques, such as MRI or any other kind of imaging technique. Other molecules can be dissolved in the ferrofluid to allow imaging with other methods, such as MRI, etc.

Alternatively, the surface of the droplet may be coated with functionalized surfactants which are able to bind a fluorescent molecule, for example, as described in CAMPAS ET AL., QUANTIFYING CELL-GENERATED MECHANICAL FORCES WITHIN LIVING EMBRYONIC TISSUES. NAT METH, 11(2):183-189, FEBRUARY 2014. Additional exemplary surfactants include those described in Leduc et al., Cooperative extraction of membrane nanotubes by molecular motors, PNAS 101:17096-17101, 2004; and also, for silicone oils, Pontani et al., Biomimetic emulsions reveal the effect of mechanical forces on cell-cell adhesion, PNAS 109: 9839-9844, 201; Lucio et al., Generation of biocompatible droplets for in vivo and in vitro measurement of cell-generated mechanical stresses, Methods in Cell Biology, Volume 125, Pages 373-390, 2015. In the case of oil based ferrofluids a variety of surfactants can be used such as DuPont™ ZONYL(™) Fluorosurfactants if the carrier is a fluorinated oil, or TRITON X™ Surfactants (Dow Chemicals) for hydrocarbon oil. Many surfactants for silicone oils can also be used and are commercially available. Some of these surfactants are not biocompatible; whenever the target material is a living system, biocompatible surfactants must be used, as described in CAMPAS ET AL., QUANTIFYING CELL-GENERATED MECHANICAL FORCES WITHIN LIVING EMBRYONIC TISSUES. NAT METH, 11(2):183-189, FEBRUARY 2014; Lucio et al., Generation of biocompatible droplets for in vivo and in vitro measurement of cell-generated mechanical stresses, Methods in Cell Biology, Volume 125, Pages 373-390, 2015.

Target Materials. Once the ferrofluid liquid of the invention has been prepared, it may be placed into the target material. The target material may comprise any soft material. "Soft material" as used herein means any liquid or flexible material, including linearly and non-linearly elastic materials, simple and complex fluids of any kind (including Newtonian and non-Newtonian fluids; viscoelastic, plastic, viscoplastic, etc.), which can be homogenous or inhomogeneous, which may be isotropic or anisotropic and which can be living or inert. An exemplary target material is a biological material. Biological materials may comprise any biological system in any conditions (in vitro, in vivo, ex vivo, etc.), including a tissue, an organ, a cell, a multicellular structure, a living tissue or organ in a living organism, or a living organism. Exemplary multicellular structures include developing embryos and tissues, both in healthy and in disease states (such as tumors), etc. In some embodiments, the biological material is a living organism, is a cultured cell or cells, or is an ex-vivo biopsy, explant, or other material derived or excised from a living organism. In some embodiments, the biological material is adult tissue, such as skin or the tissue in adult organs. In some embodiments, the target biological material is living and in other embodiments, the target biological material comprises dead biological material.

In another embodiment, the target material comprises a non-living material such as a polymer gel, of other soft materials, such as emulsions, foams, colloidal dispersions, polymer melts, liquid crystals, etc.

2. Measurements of the Mechanical/Material Properties within Target Materials The ferrofluid droplets of the invention may be utilized to measure the sample's response to an applied, controlled force. When a magnetic field is applied to the droplet, the droplet will exert a controlled stress of magnitude determined by the magnetization of the droplet (for example, determined by the amount of magnetic material present within the droplet) and the strength of the magnetic field.

Figure 3:
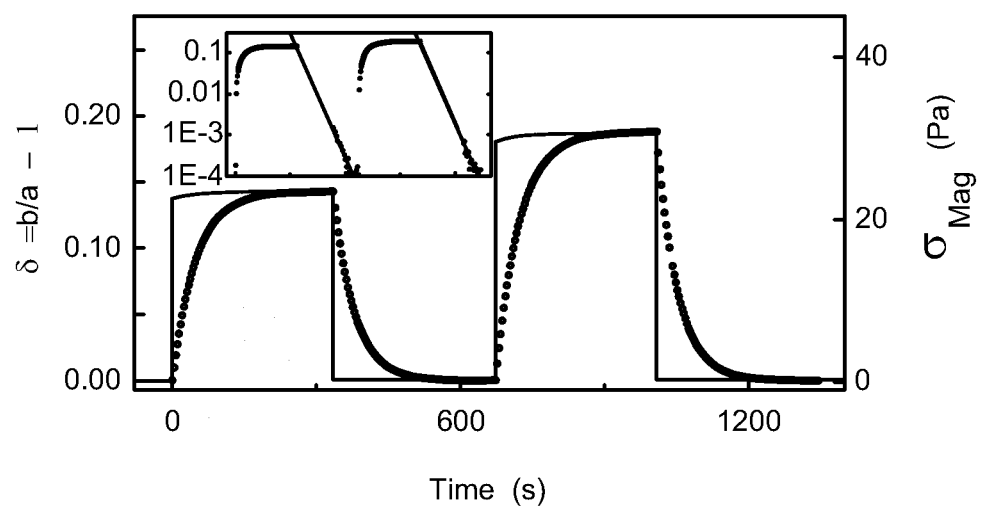
FIG. 3 depicts the deformation response of a ferrofluid droplet in an immiscible target material as a constant and spatially uniform magnetic field is alternately applied and withdrawn.
Figure 4:
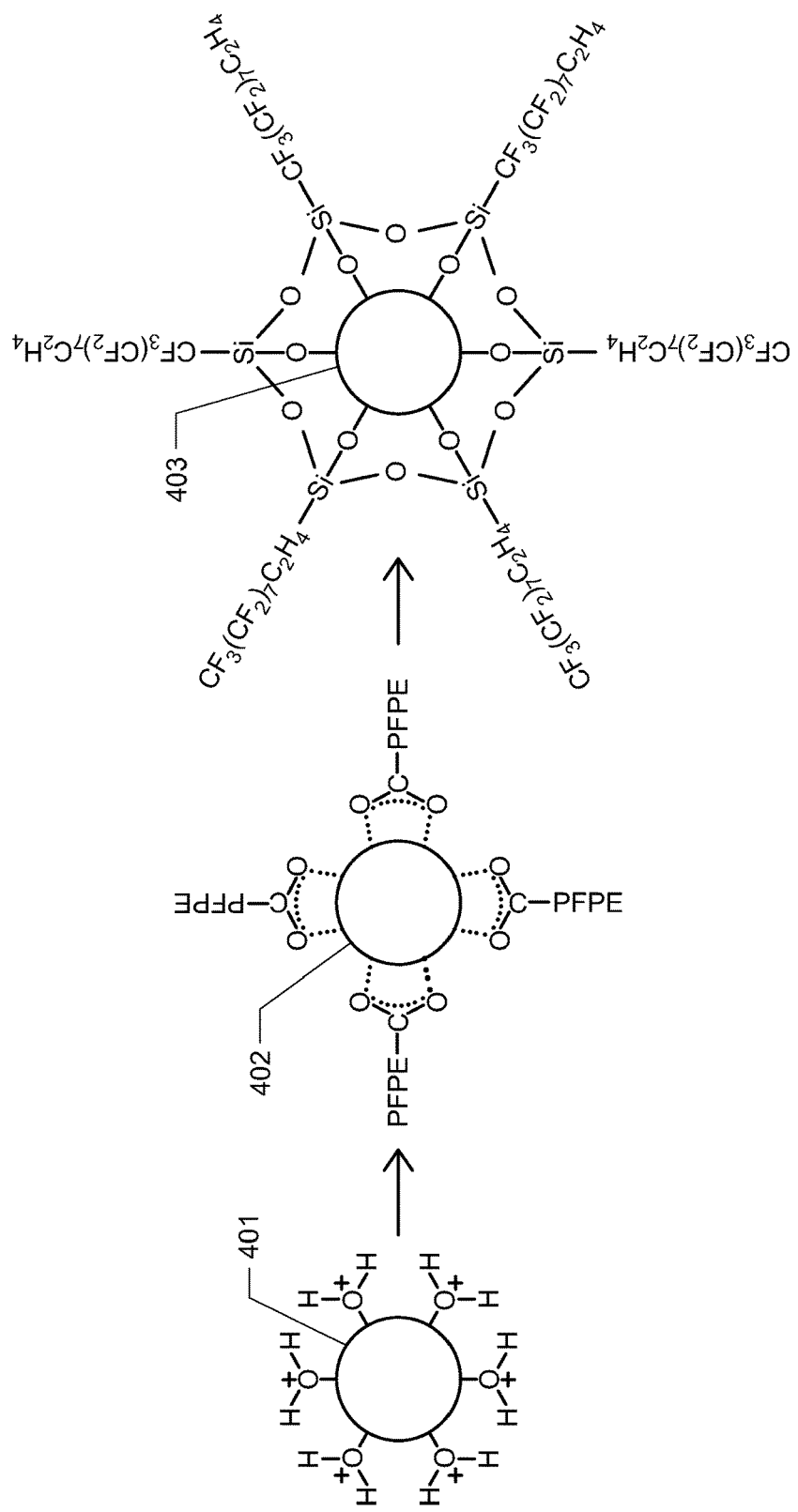
FIG. 4 depicts a two-step modification of a maghemite nanoparticle wherein fluorocarbon moieties and fluorescent moieties are conjugated to the particle to increase its solubility in fluorocarbon oil and its detectability by fluorescence microscopy.

The direction of the externally applied field will determine the direction of the extensional forces applied by the droplet to its surrounding environment. These magnetic forces and the forces to which the droplet is subjected by its surrounding environment will cause the droplet to deform. The dynamics of the droplet deformation caused by the applied magnetic field, as well as its equilibrium drop shape within the material, allow the characterization of that environment, specifically the characterization of the rheological or material properties of the material surrounding the droplet. For example, FIG. 3 depicts the response of the droplet aspect ratio to an alternating sequence wherein the magnetic field is applied for a certain period of time and then withdrawn.

This general technique may be used to characterize the rheology, structural makeup, mechanical properties, and other related physical parameters of the target material. Also, these methods allow for the measurement of the interfacial tension of the magnetic drop in the target material. This technique can therefore also be used to determine the interfacial tension of the drop.

Measurement of mechanical properties involves four basic steps. First, a ferrofluid droplet is created or placed within the target material. Second, a magnetic field is applied to the target material, creating a force exerted by the ferrofluid droplet upon its surrounding environment. The material's response to the applied force determines the degree and dynamics of the droplet deformation. Simultaneous with the second step, in a third action, deformation of the droplet is observed and quantified. Fourth, the measured response of the droplet deformation in the target material is used to characterize or profile the mechanical properties of the material surrounding the drop.

Droplet Formation in the Target Material. As a first step, to perform the mechanical measurements and various other applications of the invention, the ferrofluid liquid is created within or otherwise implanted in the target material in one or more discreet patches or droplets. This can be accomplished by various means. In one embodiment, a ferrofluid liquid droplet is created by inserting a needle (e.g. a microneedle) into the target area of the material and injecting a bolus of ferrofluid liquid through the needle, for example from a syringe or other supply of ferrofluid liquid (for example, using a microinjector), to create a droplet of desired size. With this technique, droplets may be, for example, in the range of 1 to 1000 μm in diameter, with larger sizes easily achievable. Smaller drop sizes require other methods. For instance, ferrofluid drops of tenths to hundredths of nanometers can be generated by making an emulsion of the ferrofluid with droplets of a specific size within the mentioned range, and then injecting these droplets in the target material using microinjection techniques. Drops of ferrofluid in the 1-100 microns size can also be generated using microfluidic devices, and injected afterwards using typical injection (and/or microinjection) techniques. Various methods and tools known in the art for the controllable injection of specific volumes of liquid may be used to manage the resulting droplet volume and size. Advantageously, a fine needle may be used for the injection, which can create a droplet having a diameter much larger than that of the needle. In this way, a substantial volume of ferromagnetic material may be applied to the target area while minimizing injection artifacts, which is especially useful in biological systems.

The methods of the invention have various advantages relative to magnetic tweezers. Using magnetic tweezers, there are severe limitations regarding the maximum force that can be applied, the maximum length scale that can be probed and the number of measurements which are simultaneously possible. These limitations arise mainly from geometrical constrains: injecting rigid magnetic spheres into a sample requires an injection needle with an inner diameter which is larger than the size of the magnetic sphere. As large magnetic spheres are necessary to apply the desired range of forces, the process of injection of the magnetic spheres damages the system (specially in the case of living tissues, embryos or cells). As this process damages the sample on a length scale given by the needle diameter it is difficult to apply forces on large length scales by injecting larger spheres. Typically, magnetic tweezers have been used to apply forces to single cells, with magnetic beads of about 1 micron in size. To probe e.g. living tissues, the injection needle's diameter cannot be larger than the size of a cell (and preferably much smaller to perturb minimally the system). This poses an upper limit to the bead's radius which is about $r=5$ μm for typical cell sizes. With this bead radius, magnetic tweezers cannot apply large enough forces to move the bead and therefore cannot be used to probe the mechanics of living tissues in a reliable manner. In addition, this technique cannot apply forces deep into the sample because the gradient of magnetic field strongly decreases away from the magnetic tip where it is generated. Consequently it has not been possible to probe the mechanics of tissues using magnetic tweezers. There are several other problems with the use of magnetic tweezers in living tissues (embryonic or adult) and disease processes, all of which have not permitted successful measurements of mechanics in these systems. The methods of the present invention overcome these limitations by using ferrofluid oil droplets which are injected using needles with a significantly smaller diameter than the radius of the oil droplet produced. This allows generation of larger drops with a radius of up to $r=1$ mm inside the sample without causing significant damage. Larger ferrofluid drops can be generated using standard needles if necessary for the application. The larger drop size allows application of four orders of magnitude larger net forces than is possible with magnetic tweezers, for example, reaching $F=10^{-6}$ N for a droplet with a radius of $r=50$ μm. Also, the methods in the present invention do not use gradients of magnetic fields to generate forces in the target material, but rather utilize uniform magnetic fields, which are more easily generated and controlled spatially and temporally, allowing the measurements of mechanical properties deep into tissues (or any soft material) and while the material is developing (e.g., as in embryos), rearranging and changing conformations.

The length scale at which the mechanical properties of the target material can be probed is dictated by the size of the ferrofluid droplets. Deformations of the droplets and the application of forces are effective when the magnetic stresses generated in the droplet are larger than the capillary stress, on the order of $\gamma/R$, where R is the radius of the droplet and $\gamma$ the interfacial tension with respect to the sample material. It was observed that drops with a radius $r>1$ μm can be deformed. Deformation of smaller drops is possible by lowering the interfacial tension of the drop using the methods described above. The upper limit is given by the maximum size at which ferrofluid droplets can be produced and inserted within the target material without damaging it. To prepare drops, for example, droplets with a radius between 5 μm and 50 μm, either with well-controlled sizes or with a certain distribution of sizes in the specified range, can be generated, for example as described in Generation of biocompatible droplets for in vivo and in vitro measurement of cell-generated mechanical stresses, Methods in Cell Biology, Volume 125, Pages 373-390, 2015. For example, monodispersed ferrofluid drops can be generated with standard drop microfluidic techniques, allowing control of the droplet size to a few percent tolerance. Alternatively, drops can be formed directly by injecting the ferrofluid into the sample using a pressure injector with a glass needle with matched diameter. For example, glass needles with an inner diameter ranging from 1 μm to 700 μm may be used. The diameter of resulting drops is controlled by the inner diameter of the injection needle and the pressure applied by the pressure injector.

Beyond injection, other means of introducing ferrofluid droplets to the target area may be utilized. For example, in the context of polymeric materials, the droplets may be formed and admixed with the monomers prior to their polymerization, mixed with a solution of the polymers, and/or mixed with a solution containing the polymers and a polymer crosslinking agent, such that the droplets are encased within the polymeric material upon its formation. This latter method is preferable for soft elastic materials. Also, previously formed and stabilized magnetic drops can be simply mixed and dispersed in the target material if it is a fluid or complex fluid.

For convenience, this description refers to the methods of the invention as applied to a singular ferrofluid droplet. However, it will be understood that multiple ferrofluid droplets may be utilized within a single sample. Depending on the specific application, multiple ferrofluid droplets may be placed within a target material and the arrangement of the multiple droplets may be configured to apply any desired configuration of forces to the target material. For example, a line of droplets can be used to exert force over length scales much larger than the diameter of the individual droplets. A planar arrangement of droplets can be used to exert force over an extended areal region.

Application of Magnetic Field. After the ferrofluid drop has been formed and placed into the target material, an external magnetic field is applied. In one embodiment, the applied magnetic field is a spatially uniform magnetic field, the magnitude of which can be time varying or constant. Reference herein to spatially uniform magnetic fields means magnetic fields with low spatial gradients of the magnetic field strength, such that the ferrofluid droplet does not move spatially as a consequence of the applied magnetic field. In one embodiment, the uniform magnetic field has a strength between 0.0001 and 1 T. In a constant, spatially uniform magnetic field, the magnetic field is essentially equally strong in all parts of the sample (with no or very small gradients of the magnetic field strength) and is aligned along the same spatial direction everywhere. The result of such a field being applied to a ferrofluid droplet is that the drop remains in place (it is not subject to a net force that could potentially move it, as it would occur in a magnetic field gradient) and the droplet deforms along the axis of the applied magnetic field, taking the shape of an ellipsoid of revolution along the axis defined by the direction of the magnetic field. Along this axis, the droplet will deform by extending longitudinally and shrinking in the perpendicular direction, conserving its total volume. This deformation creates a stress distribution on the surrounding material very similar to a pair of forces, or force dipole (more specifically, the stress distribution generated is dipolar for small droplet deformations and is characterized by higher order multipolar moments for larger deformations), the forces being of equal magnitude but of opposite direction. The magnitude of the magnetic stresses deforming the droplet and, thus, the stresses acting on the surrounding material, can be altered by controlling the strength of the applied magnetic field. The directionality of deformation can be altered by adjusting the direction of the magnetic field (for example, by rotating the sample holder within the magnetic field or rotating the magnetic field source relative to the sample), allowing the pair of forces or force dipole to be controllably exerted in any desired spatial direction. This use of controlled uniform magnetic fields and ferrofluid droplets to generate pairs of forces within a sample and obtain its mechanical/material properties, to the knowledge of the inventors of the present disclosure, cannot be practically achieved with any other system.

The generation of a constant magnetic field may be achieved by any means known in the art. For example, Helmholtz coils, as known in the art, comprising two solenoid electromagnets on the same axis may be used. Configurations of permanent magnets may also be used. For example, Halbach arrays or like arrangements of permanent magnets may be used to create a central area wherein a sample may reside and wherein a uniform magnetic field is present. A constant magnetic field may also be generated over a target area using the configuration described in "A horseshoe magnet for a biosensor," PCT patent application publication number WO 2014141000.

In an alternative embodiment, two ferrofluid droplets in close proximity are used instead of one, allowing the application of net forces on the magnetic drops with the application of uniform magnetic fields (no gradients of the external magnetic field are necessary). This variation of the technique uses the interaction between the induced magnetic moments in the two ferrofluid droplets. The application of a constant magnetic field on two ferrofluid droplets induces a magnetization in each of the ferrofluid droplets. The magnetic interaction between the induced magnetization of the two droplets generates an attractive force between them that squeezes the material in between them. The magnitude of the squeezing force depends on the magnitude of the applied magnetic field and the induced magnetic moments of the ferrofluid droplets.

In an alternative embodiment, the external magnetic field applied to the droplet is a magnetic field gradient. This results on a net force on the ferrofluid droplet in the direction of the gradient in the magnetic field, causing the droplet to apply a directional force pushing against the surrounding material. In this case, the drop may move in the sample depending on the material properties of the material in which the drop in embedded. To generate substantial forces in this way disadvantageously requires a very strong gradient of magnetic field, which may not be practically applied in some contexts.

In another embodiment, the magnetic field imposed upon the droplet is a combination of a spatially uniform magnetic field and a magnetic field gradient, generated and controlled either independently or in a coupled fashion.

It will be understood that the applied magnetic field may be imposed for a long period of time, or may be imposed for a short time. The field may be imposed dynamically.

The external magnetic field applied to the ferrofluid droplet is of a known magnitude and directionality. Thus, given the size and magnetization of the droplet, the droplet will exert a predictable force upon its surroundings, of known directionality. This will result in the deformation of the droplet as it interacts with surrounding structures, the direction and degree of deformation being dictated by the physical properties and configuration of materials and structures which surround the droplet. In some embodiments, the kinetics of deformation are indicative of the physical properties of the surrounding environment. Relaxation kinetics may also be quantified, wherein the magnetic field is removed or reduced and the droplet's response to this removal or lessening of the forces is observed.

In one embodiment, a series of measurements of droplet deformation and relaxation is captured (by repeated application and withdrawal of the applied magnetic field), with the magnetic field always pointing in the same direction.

In one embodiment, the source of the magnetic field, or the droplet-containing sample, or both the source and the sample, may be rotated with respect to each other, such that the axis of the magnetic field can be altered with respect to the sample. This allows for probing of the material multiple directions, allowing to determine if it is isotropic or anisotropic, and to quantify the level of anisotropy. For example, a series of measurements of droplet deformation and relaxation may captured, wherein droplet response is observed in at least two different orientations of the magnetic field axis. For example, the magnetic field axis can be applied at various orientations in order to profile the mechanical/material properties surrounding the droplet on all sides. For example, along one diameter, four, eight, 16, or more different magnetic axes may be applied, with another series of four, eight, 16 or more magnetic axes applied on a second diameter that is orthogonal to the first.

In another embodiment, two or more magnetic fields of different strength are applied consecutively, to test the response of the target material at different applied stresses and amplitudes of drop deformation.

Observation of Droplet Deformation and Relaxation. In a third action, commensurate with the application of magnetic fields to the ferrofluid droplet, the response of the ferrofluid droplet to the applied magnetic field is observed. Observation may be by any method, for example by direct visual observation via a microscope, using light transmission, reflection, differential interference contrast (DIC), phase contrast, etc., and also any type of fluorescent microscopy (e.g. epifluorescence, confocal microscopy, multiphoton microscopy and light sheet microscopy, among others). Alternatively, the droplet's shape can be measured using ultrasound scattering.

Alternatively optical techniques can be used, for example the determination of the emission modes of the droplet when it is used as a laser cavity. Alternatively, the ferrofluid material (fluorocarbon-based ferrofluid, and other types of ferrofluids) will sometimes be visible by MRI or related radiographic imaging modalities, or may be made visible to such modalities by the addition of contrast agents dissolved or dispersed in the ferrofluid. Advantageously, this allows for response observation even in opaque samples or where direct visual observation with wavelengths in the visible range is not practical.

In one embodiment, the ferrofluid liquid of the invention comprises an agent which aids in its imaging. For example, dyes or fluorophores may be included in the liquid to aid in visualizing droplets by light microscopy or fluorescent microscopy imaging systems. Also, fluorescent surfactants can be added to the droplet to visualize its surface. Alternatively, contrast agents or other materials may be included in the ferrofluid liquid to aid visualization by radiological imaging modalities. The visualization agents may be dissolved or dispersed within the liquid, or may be bound to the magnetic particles or other carrier particles dissolved or dispersed within the carrier liquid.

A series of images of the droplet, for example captured at periodic intervals of time, for example at several frames per second, can be captured as it responds to applied and withdrawn magnetic fields (or to time varying magnetic fields), the series of images being stored and used for subsequent analysis. The response of the droplet over different time scales can be measured from this sequence of images.

Calculating Mechanical Properties of the Target Material. The measured dynamics of drop deformation when a field is applied, as well as its response when the field strength changes or the field is eliminated, can be used to determine the mechanical properties of the surrounding environment. This can be performed by any mathematical analyses, as known in the art, for the derivation of mechanical properties from the response to applied forces.

In one embodiment, mechanical properties are calculated by performing creep and relaxation experiments. A sudden, constant magnetic stress may be applied to the sample target material.

The stress applied to the material is calculated as Equation 1:

$$\sigma = 1/2\ \mu_0 M(H)^2 \quad \text{Equation 1:}$$

where $\sigma$ is the stress applied, M is the magnetization at a given applied magnetic field H. As described in Ferrofluid Flow Phenomena, Thomas Franklin, Master thesis, MIT 2003, the magnitude of the magnetization can be estimated using Langevin's theory, Equation 2:

$$M = M_s(\text{Coth}(\alpha) - 1/\alpha) \quad \text{Equation 2:}$$

wherein M is the saturation magnetization of the ferrofluid and Coth is the hyperbolic cotangent, and wherein $\alpha$ is defined according to Equation 3:

$$\alpha = (\pi d^3 M_d \mu_0 H)/6kT \quad \text{Equation 3:}$$

wherein $M_d$ is the domain magnetization of the magnetic material, d is the nanoparticle's diameter, T is the temperature and k is the Boltzmann's constant.

The saturation magnetization of the ferrofluid may be calculated according to Equation 4:

$$M_s = \phi M_d \quad \text{Equation 4:}$$

wherein $\phi$ is the volume fraction of magnetic material to carrier liquid. The magnetization of the ferrofluid can also be measured as a function of the applied magnetic field with any other standard techniques.

Figure 1B:
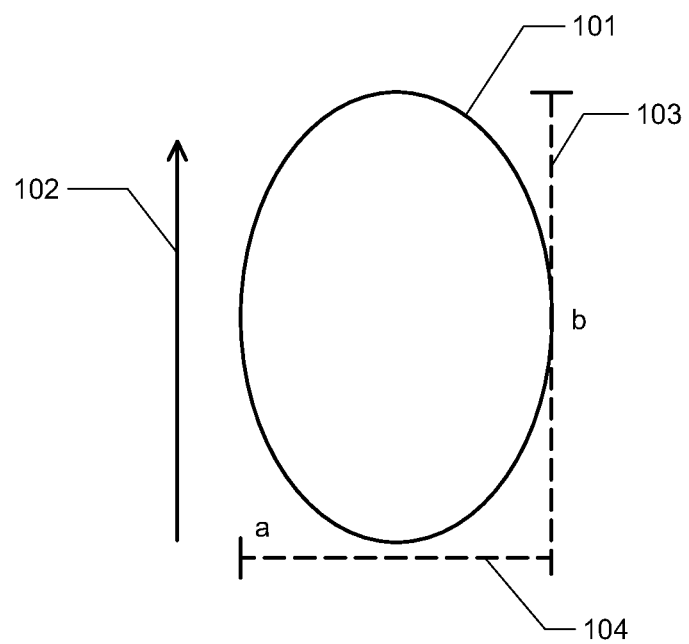
FIG. 1B depicts the same ferrofluid droplet (101) upon the application of a spatially uniform magnetic field of orientation 102. The droplet in 1B is deformed into an ellipsoid of revolution, elongated along the axis of the applied magnetic field, with a (103) being the major axis of the ellipsoid and b (104) being the minor axis of the ellipsoid.
Figure 5A:
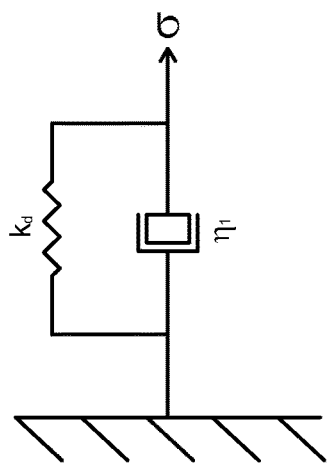
FIG. 5A depicts a dash-pot model of a target material comprising a Newtonian liquid.
Figure 5B:
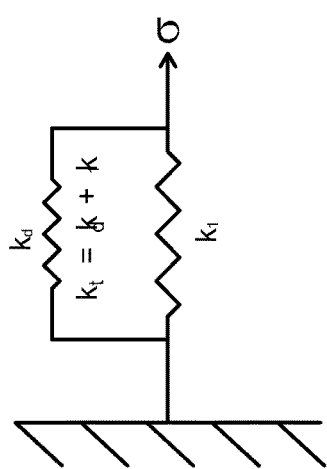
FIG. 5B depicts a dash-pot model of a target material comprising an elastic material.
Figure 5C:
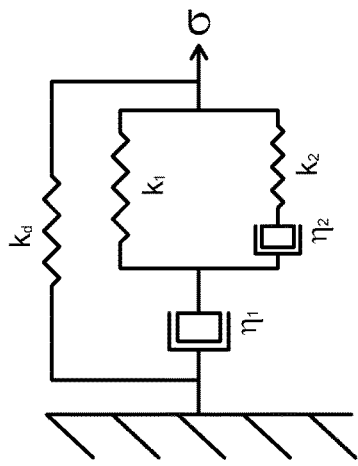
FIG. 5C depicts a dash-pot model of a target material comprising a complex material, for example, a cell or a tissue.

The dynamical behavior of the local material's strain is recorded over time. This strain is related to the droplet aspect ratio b/a (see FIG. 1) as in Equation 5:

$$\vartheta = 2/3(b/a - 1) \quad \text{Equation 5:}$$

wherein a is the major axis and b is the minor axis of the elliptically deformed droplet. To be able to obtain material properties of any soft material the strain response $\vartheta(t)$ to an applied stress $\sigma$ may be modeled using a simple 1-dimensional framework consisting of dashpots representing viscous elements $\eta_i^{1D}$ and springs representing elastic elements $k_i^{1D}$, for example as depicted in FIGS. 5A, 5B, and 5C, for different models of target material. This simplification becomes possible because the interfacial tension of the magnetic droplet can be incorporated into this framework as a spring in parallel to the material's mechanical properties. The spring constant is given by Equation 6:

$$k_d = 6\sigma_\gamma = 6\gamma/R \quad \text{Equation 6:}$$

wherein $\gamma$ is the interfacial tension between the droplet and its environment and R is the droplet radius, prior to its deformation by the magnetic field, for example as set forth by Style et al., Surface tension and the mechanics of liquid inclusions in compliant solids, Soft Matter 11:672-679, 2015].

Modeling the mechanical properties of complex viscoelastic materials with one dimensional mechanics models has the key advantage that the approach is very general and that dynamical solutions for the model can be found analytically. This allows the determination of material properties using the following workflow: In a first step, $\vartheta(t)$ is measured as a response to a sudden application of $\sigma$ in a creep experiment (turn on external magnetic field to a constant value), or a sudden release of $\sigma$ in a drop relaxation experiment. In a second step, the material's mechanical properties are described by a 1-dimensional mechanics model using dashpots and springs. The expected strain response $\vartheta(t)$ is found by solving this model analytically. Third, the experimentally obtained creep/relaxation curves are fitted with predicted temporal response of the strain $\vartheta(t)$ and, from the fit parameters, quantitative values for the model elements $\eta_i^{1D}$ and $k_i^{1D}$ are obtained. In a last step the magnitudes of the model elements $\eta_i^{1D}$ and $k_i^{1D}$ are converted to the material's Young moduli $E_i$ and viscosities $\eta_i^{3D}$ via Equation 7:

$$E_i = 5/12 k_i^{1D} \quad \text{Equation 7:}$$

and Equation 8:

$$\eta_i^{3D} = 5/36 \eta_i^{1D} \quad \text{Equation 8:}$$

The interfacial tension of the droplet with respect to its environment is deduced from the corresponding spring of the 1D model as Equation 9:

$$\gamma = 1/6 R k_d.\qquad\text{Equation 9:}$$

All mechanical parameters of the target material can be quantitatively measured in this way, as well as the interfacial tension (and the viscosity) of the ferrofluid drop in the target material. This method can be thus used as a tensiometer for fluids that can be actuated magnetically, and has several advantages over conventional tensiometers, such as the small sample volume necessary to make a measurement and the fact that it can measure extremely low interfacial tensions (below 0.05 mN/m).

Materials can be modeled for example using a combination of springs corresponding to elastic elements and dashpots representing viscous elements. These two building blocks can be combined either in series of in parallel. For example, tissue can be modelled using a dash-pot corresponding to the viscosity of the tissue $\eta_1$ in series with a spring given by the tissue's elastic modulus $k_1$, as depicted in FIGS. 5A, 5B, and 5C. The viscosity $\eta_2$ and elastic modulus $k_2$ of individual cells can be added to the model as a Maxwell term in parallel to $k_1$. The values of $\eta_1$, $\eta_2$, $k_1$, $k_2$ are obtained as described above.

Manipulating Properties of the Target Material with Applied Forces

In one embodiment, the response of target material, e.g. a biological system, to mechanical forces applied using the tools and methods of the invention can be studied. For example, forces can be selectively applied for long or short time scales to a specific biological system (e.g. a developing embryo, tumor, etc.) and subsequent biological responses can be monitored, such as changes in morphology, gene expression, etc. Advantageously, the inert droplets appear to be minimally disruptive in living cells, cell aggregates, and tissues, allowing them to develop and grow normally.

In another embodiment, the forces applied using the ferrofluid droplets of the invention are used to manipulate biological processes, wherein a force, known to have a specific biological effect, is applied by applying a magnetic field to a droplet present in the biological system, to impart the specific biological effect. In one embodiment, the flow of materials within living systems can be manipulated by placement of ferrofluid droplets at control points and the application of forces may be used to divert or enhance flow to or from a region.

In another embodiment, the flows or rearrangements of inert soft materials, such as polymer melts, can be induced and controlled by the application of magnetic fields to magnetic drops embedded in the sample.

3. Devices of the Invention

The invention further encompasses devices for applying magnetic fields and imaging ferrofluid droplets as they respond to magnetic fields. In one embodiment, the invention comprises a device comprising a sample chamber. The sample chamber holds a sample (either living or inert) comprising a target material, in which one or more ferrofluid droplets are present. The device further comprises magnetic field source. The device is configured such that the relative position of the magnetic field source and the sample chamber may be controllably adjusted, such that the sample is subjected to a magnetic field of known strength, based on the position and distance to the magnetic source, and the orientation of the magnetic field source. The device is configured such that the sample in the sample chamber can be continuously imaged by an imaging modality, such as a light microscope, a confocal microscope, MRI imaging or other imaging modality. The imaging modality captures images of the one or more droplets in the sample. The angle of the sample chamber to the imaging modality can optionally be altered, such that the one or more droplets can be imaged from multiple planes of view. The apparatus described above may advantageously be configured with a mounting ring such that it may be fitted onto a standard microscope.

Figure 2:
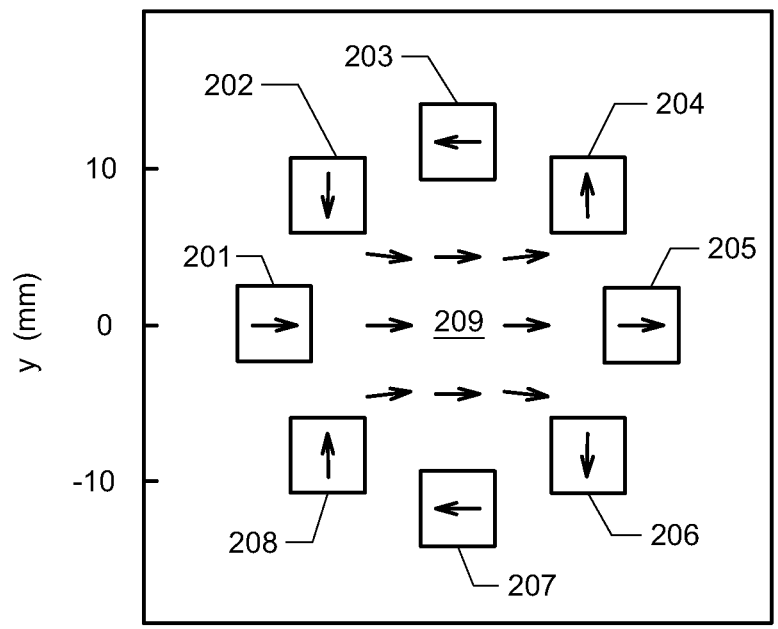
FIG. 2 depicts an array of cubic magnets (201-208) each having an orientation (e.g. north pole to south pole) indicated by the arrow. Multiple lines indicating the directionality of the magnetic field created by the array are depicted within the interior space (209) of the array, the field being highly uniform therein.

In one embodiment, the invention comprises a magnetic source comprising an array of permanent magnets. The magnets are present in a novel configuration, as depicted in FIG. 2, wherein the arrows indicate the polarity of the magnetic field in each magnet in the central region surrounded by the magnet. This configuration of permanent magnets is capable of generating very strong, unidirectional and largely uniform magnetic fields in the central area where the sample is placed. The configuration of magnets is arranged such that a central space exists within the uniform magnetic field and wherein samples may be placed in this central space, and wherein an imaging modality can image ferrofluid droplets within the sample. For example, a the magnet configuration may comprise a Halbach array or like array of permanent magnets and may be attachable to a microscope stage with the central sample region located within the field of view. The microscope stage may be configured such that the sample remains in a fixed position within the field of view of the microscope and the magnet array can be controllably raised and/or lowered such that the intensity of magnetic field around the sample can be manipulated.

In another embodiment, the invention comprises a software program. The software program performs, in a computing environment, multiple operations. The software may be configured to identify a ferrofluid droplet within an in image, analyze multiple, serial images of the ferrofluid droplet, and calculate the forces applied by such droplet based on the known magnetization, parameters of applied magnetic field, and the known viscosity. The software also analyzes the shape of the droplet and its changes over time in response to the magnetic field, and extracts the rheological or material properties of the surrounding material from this analysis and other analysis of the droplet. Hundreds of droplets may be monitored and analyzed in parallel by the software.

4. Magnetic Stir Bar

In one embodiment, the invention comprises a method of rotating continuously a ferrofluid droplet within a target material. The rotation is effected by exposing the ferrofluid droplet to rotational magnetic fields which both deform and continuously rotate the droplet, for example at 1-100 RPM. If sufficient rotational force is applied to the droplet for it to overcome the friction of the surrounding material, the droplet can be caused to rotate within the material. In this way, a ferrofluid droplet advantageously may be used to create a vortex, eddy, or other motion capable of mixing small volumes of liquid or any other fluids (Newtonian and complex fluids) in the surrounding space, for example at the scale of 5 microns and larger scales. For example, the ferrofluid droplet may be used as a magnetic stir bar for the mixing of liquids within a microfluidic device. In a biological context, the ferrofluid droplet may be used to mix compounds in a fluidic volume, such as within a cell or tissue, for example in the context of drug delivery, delivering agents evenly to a biological structure, for example therapeutic compounds, contrast agents, or other materials. In yet another example, the rotational forces applied to a ferrofluid droplet are used to disrupt or destroy surrounding structures. For example, a ferrofluid droplet placed within a tumor or tumor cell and could be used to destroy or disrupt the tumor cell or tumor. The magnetic stir bar may also be used to mix very small volumes (e.g. nl to microliters to ml) in reaction vessels, microfluidic chambers, and other small volumes. It may also be used to locally perturb, destroy or mix soft materials, such as polymer melts or any other kind of fluid or elastic material.

5. Application of Net Forces

In one embodiment, a magnetic field gradient is applied to a sample comprising a target material and one or more ferrofluid droplets. This results in the application of net forces to the target material, and the application of magnetic tweezer techniques and analyses, as known in the art.

6. Deforming Droplets with Electric Fields

In an alternative implementation of the invention, liquid droplets with a different electric permittivity than the surrounding material are utilized in place of ferrofluid drops in the target material. Electric fields are then applied to the target material, for example spatially uniform electric fields having a directionality. The charged droplets will then deform, and the resulting dipole forces generated by the deformed droplet can be derived based on the permittivity of the droplet, size of the droplet, and the strength of the applied electric field. The same methods disclosed above for ferromagnetic droplets can then be used to estimate the properties of the surrounding target material.

In one embodiment, a Giant Unilamellar Vesicle containing a charged solution in its interior is inserted in the target material. Upon the application of a uniform electric field, the vesicle will deform and apply mechanical stresses on its surrounding material. The temporal response of the vesicle deformation when an electric field is applied or withdrawn would allow the characterization of the material properties surrounding the vesicle, in the same way as described above for ferromagnetic drops actuated by magnetic fields.

7. Examples

Example 1

Creating Ferrofluid Droplets

Maghemite nanoparticles (Fe2O3) with an average diameter of 7 nm were utilized. To dissolve the particles within fluorocarbon oil without aggregation, particle surfaces were modified with fluorocarbon molecules as depicted in FIG. 5, as described in Zimney et al., DESIGN OF A FLUORINATED MAGNETO-RESPONSIVE MATERIAL WITH TUNEABLE ULTRASOUND SCATTERING PROPERTIES. J. MATER. CHEM. B, 2:1285-1297, 2014. In another test, a commercially available magnetite nanoparticles (DFF1 particles, by Ferrotec) with a saturation magnetization of $M_{sat}=27*10^3$ A/m were used.

The carrier fluid for the magnetic material was NOVEC 7300(™) fluorocarbon oil (by 3M). The surface tension of the oil droplets was tuned by modifying the particles with a fluorinated PEG surfactant (Krytox-PEG; Ran biotechnologies) at 2% w/w. Use of the surfactant lowered the surface tension of the ferrofluid droplets to about 3 mN/m. The magnetic particles were loaded in the carrier fluid at a volume ratio of 6%.

Example 2

Device for Measuring Droplet Deformation

Magnetic fields were generated using an array of 8 cubic NdFeB permanent magnets (5 mm per side), configured as depicted in FIG. 2. A portable module was constructed to hold the magnets in place, the module being mounted to a standard inverted microscope using an adapter. Samples were placed within the homogeneous magnetic field in the center of the magnet array, which area was also open to viewing by the scope. The module was made compatible with most inverted microscopes (including epifluorescence, confocal, and 2-photon microscopes) of different vendors. The module can be further adapted to scopes of different vendors by simply changing the adapter ring that connects it to the condenser mount on the microscope. The module was adapted to two Zeiss microscopes: an inverted scope with epifluorescence and an inverted laser scanning confocal microscope (Zeiss LSM 710). The module was fully motorized, allowing the magnets that apply the magnetic fields to be moved up/down and rotated by means of a linear vertical motor and a rotatory motor.

Example 3

Analysis Software

The measurement of mechanical properties requires knowledge of the applied stress and the resulting strain as a function of time. A software program was developed to control the position of the magnets with respect to the sample, controlling the intensity of the magnetic field and, therefore, the applied stress, was developed. The software also provided analysis of the strain induced in the samples by analyzing aspect ratio while the images are acquired.

The software was written in LABVIEW(™) (National Instruments). To simplify the control of the device as much as possible a game pad controller (Logitech) was used to control the interface.

Example 4

Measuring Mechanical Properties of a Bulk Material

Ferrofluid droplets with radii 30 μm<r<200 μm created by injecting ferrofluid into 3 different polymeric NIST-traceable viscosity references, were used to calibrate the technique. A constant magnetic stress was applied, at which the steady-state aspect ratio is a direct readout of the capillary stress (drop interfacial tension). The magnetic stress was removed, and the capillary stress forces the drop to relax back to the spherical shape. The relaxation of the aspect ratio has been found theoretically to be a single exponential decay, where the time constant is, up to a geometrical factor, η/γc. The viscosities of the three standards were measured over the range 40 Pa s<η<1500 Pa s to excellent agreement with the reference values (1% relative error between the measure values and the reference values). The precision and accuracy of this in situ technique was comparable to state-of-the-art bulk rheometry. In addition, the interfacial tension between the two fluids, calculated from the capillary stress, was shown to agree well with measurements from a pendant-drop tensiometer, with comparable precision and requiring much smaller volumes (μL vs. mL). The invention described herein also provides a good method to measure interfacial tension between fluids at very small scales. Specially, this technique can measure very low interfacial tensions (below 1 mN/m), which is difficult to do with other available techniques, such as the pendant drop tensiometer.

Example 5

Measurement of Material/Mechanical Properties in Living Cells

Ferrofluid droplets, composed as described above, were formed inside the blastomeres (cells) of living zebrafish embryos at the 8-16 cell blastula stage. Ferrofluid was injected into the blastomeres (cells) using a glass needle with a 10 μm inner diameter, forming droplets of about 20-50 nm in diameter. Using the device described above in Example 2, magnetic fields were applied and withdrawn and the deformation of the droplet was monitored by measuring aspect ratio at different time points. Using the known properties of the droplets and the change in aspect ratio, the internal mechanical properties of the cells were measured, for example the viscosity of the embryonic tissue was estimated at $10^5$ Pa s.

Example 6

Micron-scale Magnetic Stirbar in Biological Material

A magnetic stirbar was created by introducing ferrofluid droplets of about 50 μm diameter into a zebrafish embryo. A rotating, homogeneous magnetic field was applied, using the device of Example 2, rotating at several RPM. In response, the droplets were deformed and the droplets rotated, creating a localized vortex in the embryo.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of applying a force of known magnitude within a liquid or elastic material, wherein the liquid or elastic material is a biological material, comprising the steps of selecting a force magnitude to be applied to the liquid or elastic material and a directionality of the applied force;

introducing a ferrofluid droplet into the liquid or elastic material, the ferrofluid droplet comprising a magnetic material dissolved or dispersed within a carrier liquid, wherein the carrier liquid is inert to and immiscible with the material, wherein the volume of the ferrofluid droplet and magnetization of the ferrofluid droplet are known; and applying a homogeneous magnetic field of selected magnitude to the liquid or elastic material, of such magnitude that the ferrofluid droplet is deformed along an axis of the applied magnetic field, wherein the magnitude of the homogeneous magnetic field is selected such that the force applied by poles of the deformed droplet equals the force magnitude selected to be applied to the liquid or elastic material, and wherein the directionality of the applied magnetic field is selected to induce deformation of the droplet in the selected directionality of the applied force.

2. The method of claim 1, wherein
the biological material is selected from a group consisting of a cell, an aggregation of cells, an embryo, embryonic tissue, adult tissue and a living organism.

3. A method of measuring viscosity or elastic modulus of a material comprising a liquid or elastic biological material, wherein the liquid or elastic biological material comprises an inside of a cell, an aggregation of cells, an embryo, embryonic tissues, or a tumor, the method comprising introducing a ferrofluid droplet of radius R into the liquid or elastic biological material, the ferrofluid droplet comprising a magnetic material dissolved or dispersed within a carrier liquid, wherein the carrier liquid is chemically inert to and immiscible with the liquid or elastic biological material, wherein the magnetization of the ferrofluid droplet is known according to the composition and size of the droplet; and applying a homogeneous magnetic field of known strength to the liquid or elastic biological material, of such magnitude that the ferrofluid droplet is deformed along an axis of the applied magnetic field;

measuring an aspect ratio of the deformed droplet after it has reached an equilibrium deformation;

removing the magnetic field and monitoring the aspect ratio of the droplet as it returns to a substantially spherical shape and calculating a change in droplet deformation vs. time for such relaxation;

utilizing the known magnetization of the droplet and the known magnetic field strength and the observed relaxation dynamics of the aspect ratio of the droplet in response to the removal of the magnetic field to calculate an interfacial tension between the droplet and the liquid or elastic biological material, the viscosity of the liquid or elastic biological material, or the elastic modulus of the liquid or elastic biological material.

* * * * *